United States Patent
Nakao et al.

(10) Patent No.: US 8,162,870 B2
(45) Date of Patent: Apr. 24, 2012

(54) BLOOD FILTER DEVICE AND METHOD OF PRODUCING THE SAME

(75) Inventors: Shota Nakao, Hiroshima (JP); Yutaka Katsuno, Hiroshima (JP); Masayoshi Omori, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 527 days.

(21) Appl. No.: 12/223,242

(22) PCT Filed: Jan. 19, 2007

(86) PCT No.: PCT/JP2007/050789
§ 371 (c)(1),
(2), (4) Date: Jul. 25, 2008

(87) PCT Pub. No.: WO2007/086322
PCT Pub. Date: Aug. 2, 2007

(65) Prior Publication Data
US 2010/0179465 A1 Jul. 15, 2010

(30) Foreign Application Priority Data

Jan. 27, 2006 (JP) .................. 2006-019086
Feb. 17, 2006 (JP) .................. 2006-041416
Apr. 7, 2006 (JP) .................. 2006-106299

(51) Int. Cl.
*A61M 1/16* (2006.01)
*B32B 37/12* (2006.01)
(52) U.S. Cl. ............... 604/6.09; 156/325; 210/456
(58) Field of Classification Search .......... 210/445, 210/493.1, 436, 472; 604/6.09; 156/325
See application file for complete search history.

(56) References Cited

U.S. PATENT DOCUMENTS

| | | | | |
|---|---|---|---|---|
| 4,304,670 A | * | 12/1981 | Watanabe et al. | ............ 210/446 |
| 6,143,174 A | | 11/2000 | Graus | |
| 2004/0195165 A1 | * | 10/2004 | Bernard et al. | ......... 210/321.89 |

FOREIGN PATENT DOCUMENTS

| | | | |
|---|---|---|---|
| EP | 1 607 110 A1 | | 12/2005 |
| EP | 1607110 A1 | * | 12/2005 |
| GB | 1440027 | | 6/1976 |
| JP | 6-205828 A | | 7/1994 |
| JP | 10-314300 A | | 12/1998 |
| JP | 11-137671 A | | 5/1999 |
| JP | 11-206877 A | | 8/1999 |
| JP | 2004-249087 A | | 9/2004 |
| WO | WO 2004/084974 A1 | | 10/2004 |

* cited by examiner

*Primary Examiner* — Nam Nguyen
*Assistant Examiner* — Denise R Anderson
(74) *Attorney, Agent, or Firm* — Hamre, Schumann, Mueller & Larson, P.C.

(57) ABSTRACT

A blood filter device has a housing that includes: a head portion (2) provided with a blood inlet (5) and forming an upper structure of the housing, a filtration portion (3) positioned below the head portion and forming a middle structure of the housing, and a bottom portion (4) disposed below the filtration portion and provided with a blood outlet (7); and a filter (8) mounted in a cavity of the filtration portion and partitioning a cavity of the housing into a head portion side and a bottom portion side. The filter is formed of a filter sheet folded to have a plurality of pleats, and disposed so that ridgelines of the plurality of pleats traverse respectively the cavity of the filtration portion in parallel. The bottom portion has a conical portion (4a) on the inner bottom face protruding downward to form a conical face. Due to the conical portion of the bottom portion, resistance against blood passing through the housing interior is reduced, and the pressure loss can be suppressed satisfactorily while maintaining sufficient filtration performance of the filter in a small device.

15 Claims, 17 Drawing Sheets

BLOOD FILTER DEVICE AND METHOD OF PRODUCING THE SAME

TECHNICAL FIELD

The present invention relates to a blood filter device used for filtering foreign substances, thrombi, and the like in an artificial heart-lung circuit. The present invention relates also to a method of producing the blood filter device.

BACKGROUND ART

In many cases, a blood filter device such as an arterial filter is incorporated in an artificial heart-lung circuit used for heart surgery involving extracorporeal circulation for the sake of safety. To provide security for patients, it has been demanded strongly that such a blood filter device be configured so that it can remove minute foreign substances in the artificial heart-lung circuit, thrombi formed during operation, or air that has entered or been released from the circuit, so as not to allow them to enter the patient body.

A filter generally used in the blood filter device is a polyester screen filter with pores of about 20 to 40 μm. The interior of the housing serves as a path for blood in order to eliminate dust, impurities, thrombi and the like when the blood passes through the filter. For example, Patent document 1 discloses a blood filter device as shown in FIGS. 21, 22.

FIG. 21 is a cross-sectional view showing a blood filter device. A housing 1 is made of resin for example, having a head portion 2 forming an upper structure, a filtration portion 3 forming a middle structure, and a bottom portion 4 forming a lower structure. The housing 1 has a lateral cross section of a circular shape.

A blood inlet 5 is provided at a lateral face of the head portion 2. On the top of the head portion 2, an air vent 6 for discharging air such as air bubbles is provided. The head portion 2 is formed so that the inner diameter is reduced gradually toward the top of the head portion 2. This allows air bubbles to be gathered to move upward along the inner peripheral face of the head portion 2. The head portion 2 has a lateral cross section of a circular shape, and is provided with the blood inlet 5 so as to allow blood flow horizontally into the head portion 2 and along the inner wall of the head portion 2. The blood that has flowed in from the blood inlet 5 flows downwards into the filtration portion 3.

The filtration portion 3 has a cylindrical shape in which a filter 8 for filtering foreign substances in blood is disposed. The filter 8 is disposed to partition a cavity of the housing 1 into the head portion 2 side and the bottom portion 4 side. A blood outlet 7 is provided at the bottom portion 4, and thus a liquid that has flowed into the head portion 2 from the blood inlet 5 passes through the filtration portion 3 and then flows out from the blood outlet 7.

As schematically shown in FIG. 22, the filter 8 is formed of a filter sheet 8a made of a sheet-like mesh material folded to form a plurality of pleats, where ridgelines 8b of the plural pleats are aligned in a plane to have an appearance of a flat plate. Namely, an envelope of the ridgeline 8b of respective pleats is flat. The filter 8 is disposed so that the flat surface traverses the cavity of the retaining portion inner cylinder 3a (filtration portion 3), namely, the ridgelines 8b of the pleats traverse the cavity of the filtration portion 3 in parallel to each other. The ridgelines 8b of the respective pleats are oriented in parallel to the direction of the blood inlet 5 or the blood outlet 7. As a result of disposing the ridgelines 8b of the respective pleats in parallel to the direction of either the blood inlet 5 or the blood outlet 7, air bubbles can be removed easily due to the blood or a priming solution flowing in parallel to the ridgelines 8b of the pleats.

As shown in FIG. 21, a bonding resin 9 is supplied into an outer peripheral part of the filter 8, and the filter 8 is bonded to the inner peripheral face of the filtration portion 3 with the bonding resin 9.

According to this configuration, foreign substances, thrombi and the like in blood can be removed reliably, and since there are no obstacles in the vertical direction of the filter 8, air bubbles adhered onto the top face of the filter 8 during a priming operation can be removed easily by merely applying a physical impact to the housing.

Patent document 1: WO2004/084974

DISCLOSURE OF INVENTION

Problem to be Solved by the Invention

Regarding the configuration and functions of the above-described blood filter device, the following points should be taken into consideration in use:
1) being small;
2) keeping a sufficient area of filter film; and
3) reducing a pressure loss.

The device is required to be small in order to decrease the volume of the blood filter device and to reduce the priming volume of blood. Keeping a sufficient membrane area is required to maintain a sufficient filtration performance for a period as long as possible. Further, reducing the pressure loss is important from an aspect of providing a smooth extracorporeal circulation and preventing hemolysis or the like.

However, it is difficult to satisfy the above-noted conditions all at one time. For example, in an effort of providing a sufficient area of filter film in a small device, the pleat pitch of the filter should be made fine. This may cause problems such as difficulty in removal of air bubbles and an increase of pressure loss. That is, the resistance against the passing blood becomes high and the blood circulation condition deteriorates. Meanwhile, for decreasing the pressure loss while keeping a sufficient area of filter film, the filter will become larger necessarily, which will result in an increase in the priming volume of blood.

Therefore, with the foregoing in mind, it is an object of the present invention to provide a blood filter device whose housing volume is reduced to suppress the priming volume of blood, and making the pleat pitch fine so as to maintain the sufficient filtration performance, and also suppressing satisfactorily the pressure loss.

Means for Solving Problem

A blood filter of the present invention includes: a housing that includes a head portion provided with a blood inlet and forming an upper structure of the housing, a filtration portion positioned below the head portion and forming a middle structure of the housing, and a bottom portion disposed below the filtration portion and provided with a blood outlet; and a filter mounted in a cavity of the filtration portion and partitioning the cavity of the housing into a head portion side and a bottom portion side. The filter is formed of a filter sheet folded to have a plurality of pleats, and is disposed so that the ridgelines of the pleats traverse respectively the cavity of the filtration portion in parallel. In order to solve the above-mentioned problems, the bottom portion has a conical portion whose inner bottom face protrudes downwards to form a conical face.

A method of producing a blood filter device of the present invention is a method of producing a blood filter device of the above-described configuration, and the method includes: mounting the filter in the filtration portion of the housing where the bottom portion has an inner bottom face protruding downward to form a conical face, and bonding the outer peripheral part of the filter to the filtration portion with an auxiliary bonding resin; forming gaps between adjacent pleats of the filter sheets in the outer peripheral region of the filter; supplying a main bonding resin into a space between the outer peripheral part of the filter and the inner peripheral face of the filtration portion and hardening the resin at a temperature higher than room temperature so as to bond the filter to the filtration portion with the main bonding resin; and applying an outward tensile force to the both ends of each pleat due to shrinkage of the main bonding resin allowed to cool to room temperature.

Effects of the Invention

According to the blood filter device of the above-mentioned configuration, due to the conical portion at the bottom portion, resistance against blood passing through the housing is reduced, thereby suppressing the pressure loss satisfactorily while maintaining the sufficient filtration performance of the small-sized filter.

According to the method of producing the blood filter device, when the main bonding resin is allowed to cool to room temperature, the shrinkage causes an outward tensile force applied to the both ends of each of the pleats of the filter. As a result, the pleat-gaps formed in the outer peripheral region of the filter is widened to the central region, thereby holding sufficient gaps between the pleats.

EXPLANATION OF LETTERS AND NUMERALS

Figure 1:
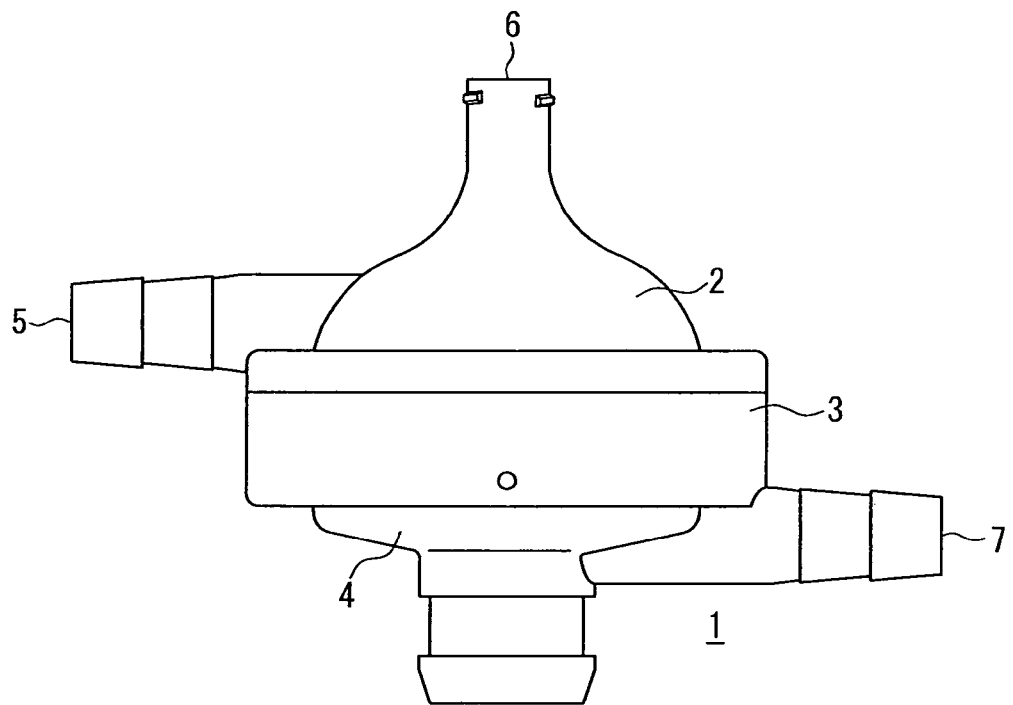
FIG. 1 is a front view showing a blood filter device according to Embodiment 1 of the present invention.

1 housing
1a upper half of housing
1b lower half of housing
2 head portion
3 filtration portion
3a retaining portion inner cylinder
3b retaining portion outer cylinder
4 bottom portion
4a conical portion
4b cylindrical portion
5 blood inlet
6 air vent
7 blood outlet
8 filter
8a filter sheet
8b ridgeline of pleat
8c pleat-gap
9 bonding resin
10,16 annular rib member
11 regulating plate
12,19 annular substrate
13 rib
14 clearance
15 slant
17 main bonding resin
18 auxiliary bonding resin
20 notch
21 through hole
22 rotating jig
22a cavity
23 resin reservoir
24 resin-supply channel

DESCRIPTION OF THE INVENTION

It is preferable in the blood filter device of the present invention configured as above that the base angle θ is set in a range of $6° \leq θ \leq 12°$.

It is also preferable that the bottom portion has a cylindrical portion connected to the filtration portion and that the conical portion is formed at the lower part of the cylindrical portion.

It is also preferable that the height of the cylindrical portion is 0.5 mm or more.

It is also preferable that the filtration portion has a cavity whose diameter Φ is in a range of 35 mm≦Φ≦65 mm.

It is also preferable that a regulating plate for annularly covering over the outer peripheral part of the filter is provided.

Further, it is possible to provide an annular rib member that is made of annular substrate disposed facing the ridgelines of the pleats in the outer peripheral region of the filter and provided with a plurality of ribs, where the ribs are inserted respectively between the adjacent pleats of the filter sheet, thereby holding gaps between the pleats of the filter sheet; and the regulating plate is formed as a result that the inner periphery of the annular substrate extends toward the center of the filter.

It is preferable that, when Ri denotes the inner diameter of the annular ring of the regulating plate covering over the outer peripheral part of the filter and Rf denotes the diameter of the effective region of the filter, 0.7 Rf≦Ri≦0.9 Rf.

It is also preferable that a clearance is formed between the upper face of the filter and the lower face of the regulating plate.

It is preferable that the clearance is in a range of 0.5 mm to 2.0 mm.

It is also preferable that the lower face of the regulating plate is slanted with respect to the upper face of the filter in a direction to increase the clearance toward the center of the filter.

It is preferable that the angle of the slant of the lower face of the regulating plate is in a range of 5 degrees to 10 degrees.

In the method of producing the blood filter device constituted above in the present invention, it is preferable that the annular rib member formed of an annular substrate on which a plurality of ribs are aligned in the circumferential direction is mounted in the filter so that the ribs are inserted respectively between the ridgelines of the plural pleats in the outer peripheral region of the filter, thereby forming gaps between the adjacent pleats of the filter sheet.

It is also preferable that the housing is made of a polycarbonate resin, and an urethane resin is used as the main bonding resin such that the thickness of the main bonding resin will be in a range of 5 to 10 mm in the radial direction of the filtration portion.

It is also preferable that the main bonding resin is hardened at a temperature in a range of 35 to 55° C.

It is also preferable that the main bonding resin is supplied up to a range including the annular rib member.

It is also preferable that the main bonding resin is supplied into the space between the outer peripheral part of the filter and the inner peripheral face of the filtration portion while applying a centrifugal force about the center of the cavity of the filtration portion.

Hereinafter, a blood filter device and a method of producing the same according to embodiments of the present invention will be described with reference to the drawings.

(Embodiment 1)

Figure 2:
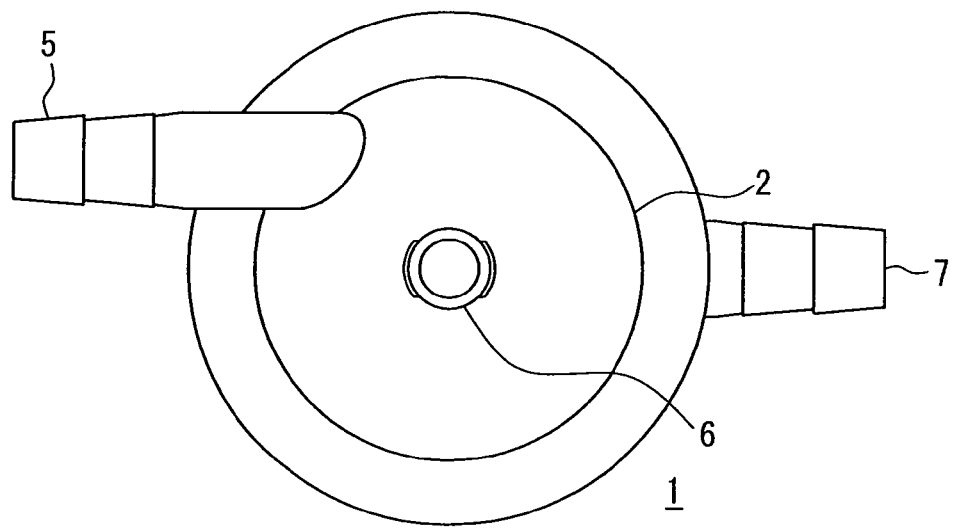
FIG. 2 is a plan view showing the blood filter device.
Figure 3:
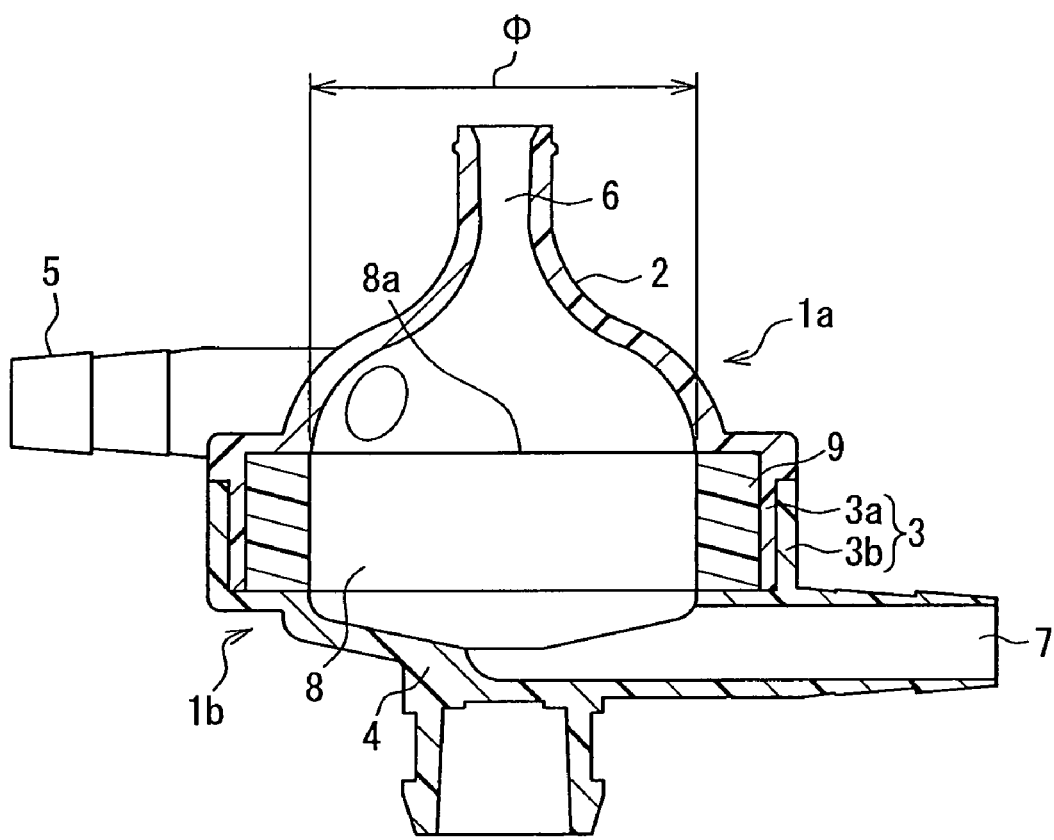
FIG. 3 is a cross-sectional view showing the blood filter device.

FIG. 1 is a front view of the blood filter device according to Embodiment 1 of the present invention, FIG. 2 is a plan view of the same, and FIG. 3 is a cross-sectional view of the same. A housing 1 is made of resin for example, and it includes a head portion 2 forming an upper structure of the housing, a filtration portion 3 forming a middle structure of the housing, and a bottom portion 4 forming a lower structure of the housing. The housing 1 has a lateral cross section of a circular shape.

At a lateral face of the head portion 2, a blood inlet 5 is provided so as to allow blood to flow into the head portion 2 horizontally and along the inner wall of the head portion 2. On the top of the head portion 2, an air vent 6 for discharging air such as air bubbles is provided. A blood outlet 7 is provided at the bottom portion 4. A filtration portion 3 has a cylindrical shape. As shown in FIG. 3, a filter 8 for filtering foreign substances in blood is disposed in the filtration portion 3. The filter 8 partitions the cavity of the housing 1 into a head portion 2 side and a bottom portion 4 side. Liquid that has flowed into the head portion 2 from the blood inlet 5 passes through the filtration portion 3 and then flows out from the blood outlet 7.

The head portion 2 is formed so that its inner diameter is reduced gradually toward the top of the head portion 2. This helps air bubbles to be gathered and to move upward along the inner peripheral face of the head portion 2. The head portion 2 has a lateral cross section of a circular shape, and is provided with the blood inlet 5 so as to allow blood flow into the head portion 2 horizontally and along an inner wall of the head portion 2. The blood that has flowed in from the blood inlet 5 flows downward into the filtration portion 3. The shape of the head portion 2 is not limited to that shown in FIG. 1 etc. as long as it is formed so that an outer diameter thereof is reduced gradually toward the air vent 6. For instance, it may have a conical shape or a funnel shape.

As shown in FIG. 3, the housing 1 is composed of an upper half 1a and a lower half 1b. The filtration portion 3 is composed of a retaining portion inner cylinder 3a and a retaining portion outer cylinder 3b formed in the upper half 1a and the lower half 1b respectively. The upper half 1a and the lower half 1b are joined together by fitting the retaining portion outer cylinder 3b into the retaining portion inner cylinder 3a, thereby obtaining the housing 1 as a single component. Furthermore, a bonding resin 9 is supplied into the filtration portion 3, more specifically, to a region of the retaining portion inner cylinder 3a at which the outer peripheral part of the filter 8 is positioned. The filter 8 is bonded to the inner peripheral face of the retaining portion inner cylinder 3a with the bonding resin 9.

Figure 4A:
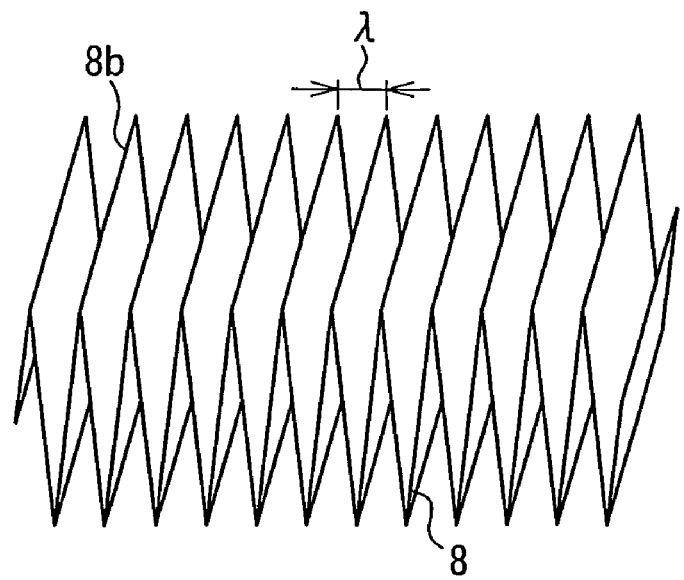
FIG. 4A is a perspective view showing a part of a filter constituting the blood filter device.

As schematically shown in FIG. 4A, the filter 8 is formed of a filter sheet made of a sheet-like mesh material folded so as to form a plurality of pleats. FIG. 4A shows only a part of the filter 8. The filter 8 is disposed so that ridgelines 8b of the plural pleats traverse respectively the cavity of the retaining portion inner cylinder 3a (filtration portion 3) in parallel. That is, a plane (envelope) including the ridgelines 8b of the respective pleats is oriented in the direction along a chord of the retaining portion inner cylinder 3a so as to be parallel to the direction of the blood inlet 5 or the blood outlet 7. Therefore, FIG. 3 shows a cross section taken along the plane parallel to the ridgelines 8b of the pleats, where the pleats are not shown. The envelope of the ridgelines 8b of the respective pleats is flat, and thus the filter 8 has an appearance of a flat plate as a whole.

Figure 4B:
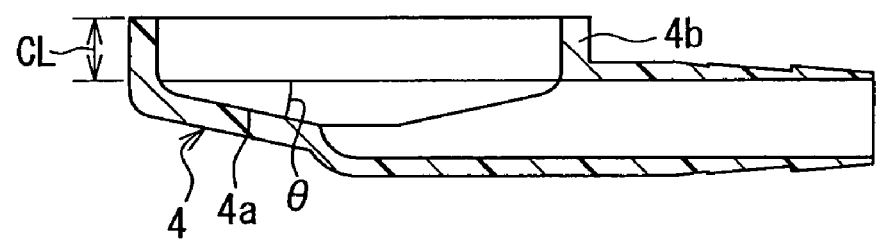
FIG. 4B is a cross-sectional view showing a bottom portion of a housing constituting the blood filter device.

FIG. 4B shows the details of the configuration of the bottom portion 4. In the blood filter device of the present embodiment, the bottom portion 4 is composed as a combination of the conical portion 4a and the cylindrical portion 4b. Therefore, the inner bottom face of the bottom portion 4 formed with the conical portion 4a has a conical face protruding downward. This conical face is effective in reducing the pressure loss of the blood flow. The pressure loss is preferred to be 7.98 kPa or lower in practical use, and more preferably 6.65 kPa or lower. The target value of the pressure loss can be attained easily by forming the conical portion 4a. The pressure loss can be reduced further by providing a structure as a combination of the conical portion 4a and the cylindrical portion 4b as shown in FIG. 4B. However, since the priming volume of blood is increased when the cylindrical portion 4b is provided, it is desirable that the conical portion 4a is provided alone or the height of the cylindrical portion 4b is as small as possible.

In the thus constituted blood filter device of the present embodiment, the pressure loss caused by the blood flowing from the blood inlet 5 and passing through the filter 8 of the filtration portion 3 is suppressed to a satisfactorily practical range. That is, it will be possible to suppress the pressure loss satisfactorily while decreasing the volume of the housing 1 to reduce the priming volume of blood and also making the pleat pitch fine in order to maintain the sufficient filtration performance.

Hereinafter, the effects realized by providing such a conical portion 4a will be described with reference to the experimental result. As shown in FIG. 4B, the base angle of the conical portion 4a is set to θ° and the height of the cylindrical portion 4b is set to CL mm. As shown in FIG. 4A, the pleat pitch of the filter 8 is set to λ mm.

Figure 5:
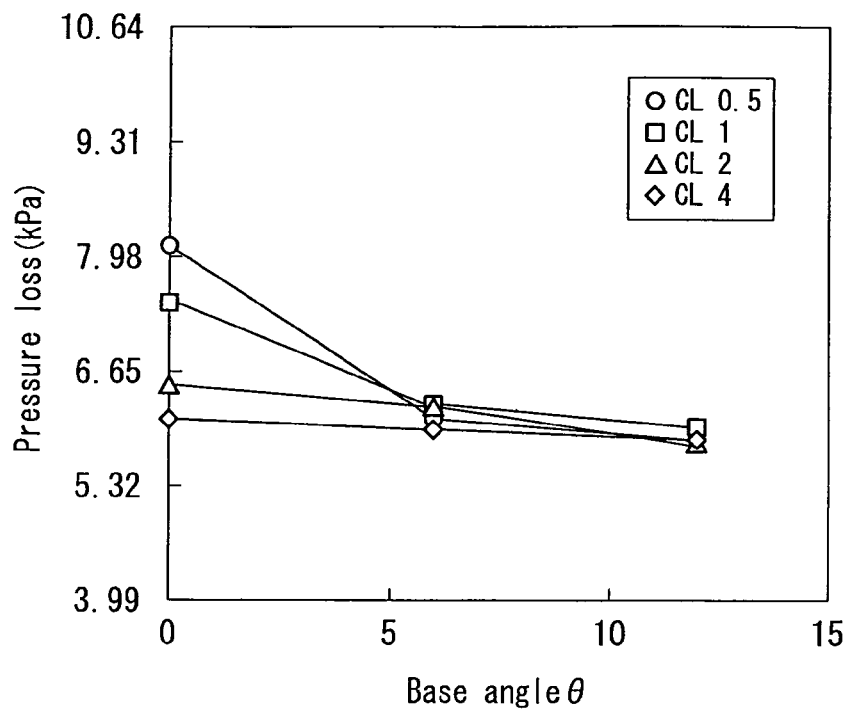
FIG. 5 is a graph indicating the relationship between a base angle θ of the bottom portion of the housing constituting the blood filter device, and a pressure loss.

FIG. 5 indicates a change in the pressure loss incident to the change of the base angle θ. The relationship between the base angle θ and the pressure loss was measured for each case where the height CL of the cylindrical portion 4b was 0.5 mm, 1 mm, 2 mm and 4 mm. When the base angle θ is 0°, the pressure loss is 6.65 kPa or lower for a blood filter device with the height CL being 2 mm or 4 mm, which does not cause any substantial problems in use. However, it is clearly shown that in a blood filter device whose height CL is 0.5 mm or 1 mm, the pressure loss is as large as approximately 7.98 kPa. Contrarily, when the base angle θ is 6° or more, the pressure loss is suppressed to 6.65 kPa or lower even when the height CL is 0.5 mm or 1 mm.

Figure 6:
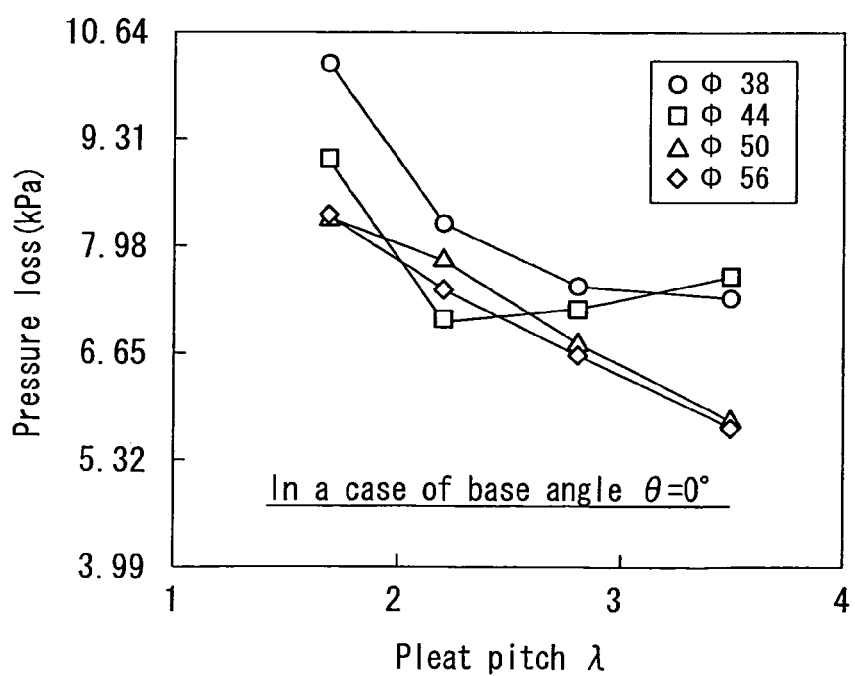
FIG. 6 is a graph indicating the relationship between a pleat pitch λ of the filter and the pressure loss when the base angle θ of the bottom portion of the housing constituting the blood filter device is 0°.

FIG. 6 shows a change in the pressure loss with respect to the pleat pitch λ when the base angle θ is 0°. The relationship between the base angle θ and the pressure loss was measured for each case where the diameter Φ of the cavity of the filtration portion 3 was 38 mm, 44 mm, 50 mm and 56 mm. FIG. 6 indicates that when the base angle θ is 0°, the pressure loss exceeds 7.98 kPa as the pleat pitch λ becomes finer.

Figure 7:
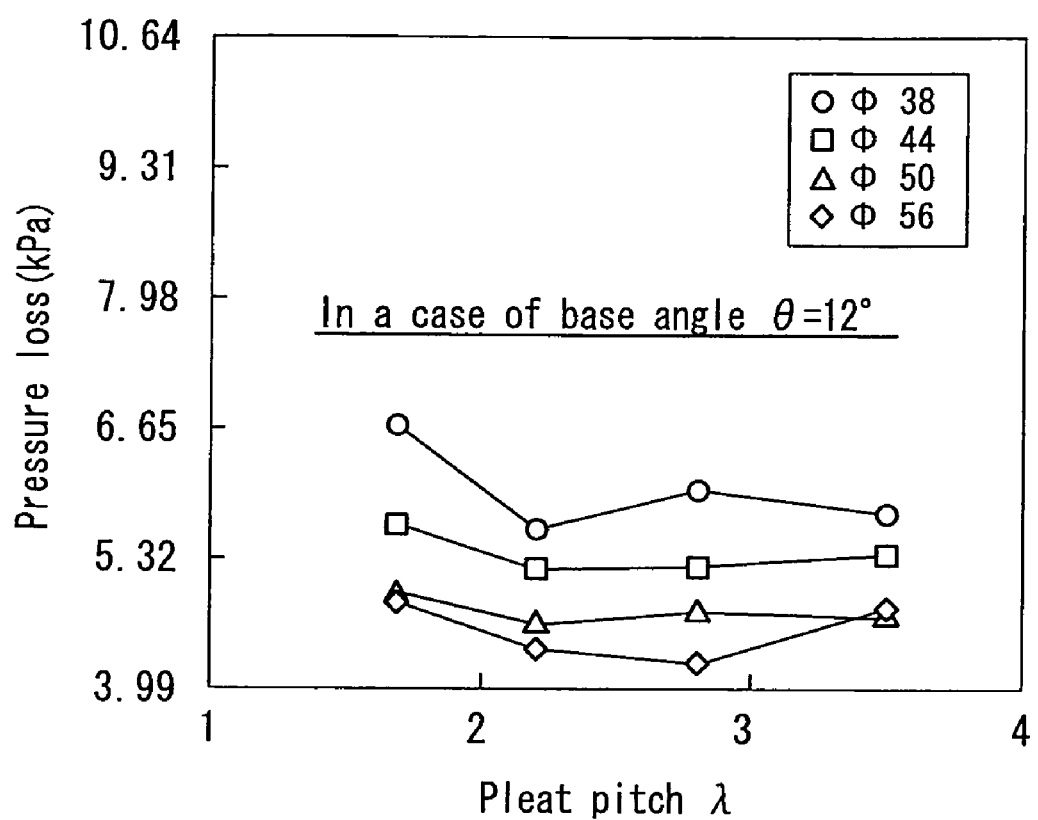
FIG. 7 is a graph indicating the relationship between a pleat pitch λ of the filter and the pressure loss when the base angle θ of the bottom portion of the housing constituting the blood filter device is 12°.

FIG. 7 indicates a change in the pressure loss with respect to the pleat pitch λ when the base angle θ is 12°. Similarly to the case shown in FIG. 6, the relationship between the pleat pitch λ and the pressure loss was measured respectively for each case where the diameter Φ of the cavity of the filtration portion 3 was 38 mm, 44 mm, 50 mm and 56 mm. FIG. 7 indicates that when the base angle θ is 12°, the pressure loss is suppressed satisfactorily (approximately 6.65 kPa or lower) even when the pleat pitch λ becomes fine within a practical range.

The above results indicate that it is effective to provide a conical portion 4a having at least a certain base angle θ in order to decrease the height CL of the cylindrical portion 4b thereby suppressing the supply of blood, and to realize a fine pleat pitch λ, thereby maintaining the sufficient filtration performance, and also to suppress satisfactorily the pressure loss. The measurement result regarding the diameter Φ of the cavity of the filtration portion 3 in a range 35 mm≦Φ≦65 mm that is preferred practically indicates that the pressure loss can be suppressed to a practically desirable range by setting the base angle θ to a range of 6°≦θ≦12°.

Furthermore, if conditions such as the priming volume of blood permit, it is possible to employ a configuration in which a cylindrical portion 4b connected to the filtration portion 3 is provided and a conical portion 4a is formed at the lower part of the cylindrical portion 4b, as shown in FIG. 4B. Even when the conical portion 4a is not formed, the cylindrical portion 4b may serve to reduce the pressure loss. When the height CL of the cylindrical portion 4b is 0.5 mm or more, a significant effect of reducing the pressure loss can be obtained.

In the present embodiment, a mesh material, a woven material, a non-woven material, or the like or a combination thereof can be used as the filter member. The filter member can be made of polyester, PET (polyethylene terephthalate), polypropylene, polyamide, fluorocarbon fiber, stainless steel or the like. The same can be applied to the following embodiments.

It is preferable that the housing 1, especially a horizontal cross section of the head portion 2, has a circular shape. However, similar effects can be obtained even when the cross section is elliptic or the like. The vertical shape of the head portion 2 is not limited to the shape as shown in FIG. 3 as long as the outer diameter is reduced gradually toward the air vent 6. For instance, it may have a conical shape or a funnel shape.

The range for supplying with the bonding resin 9 is adjusted on the basis of the inner periphery lower end of the head portion 2. That is, the inner peripheral face of the bonding resin 9 is set to coincide with the diameter of the lower edge of the inner peripheral face of the head portion 2 (and with the diameter of the cylindrical portion 4b of the bottom portion 4). Accordingly, a channel in the filter 8 defined by the bonding resin 9 continues smoothly from the lower edge of the inner peripheral face of the head portion 2 to the upper end of the cylindrical portion 4b of the bottom portion 4, and thus a smooth channel is obtained.

(Embodiment 2)

The basic configuration of the blood filter device in Embodiment 2 is the same as that shown in FIGS. 1-3. Namely, the blood filter device in the present embodiment has a configuration similar to what is shown in the front view and the plan view of FIGS. 1 and 2. The configuration of the filter is also similar to what is shown in FIG. 22.

Figure 8:
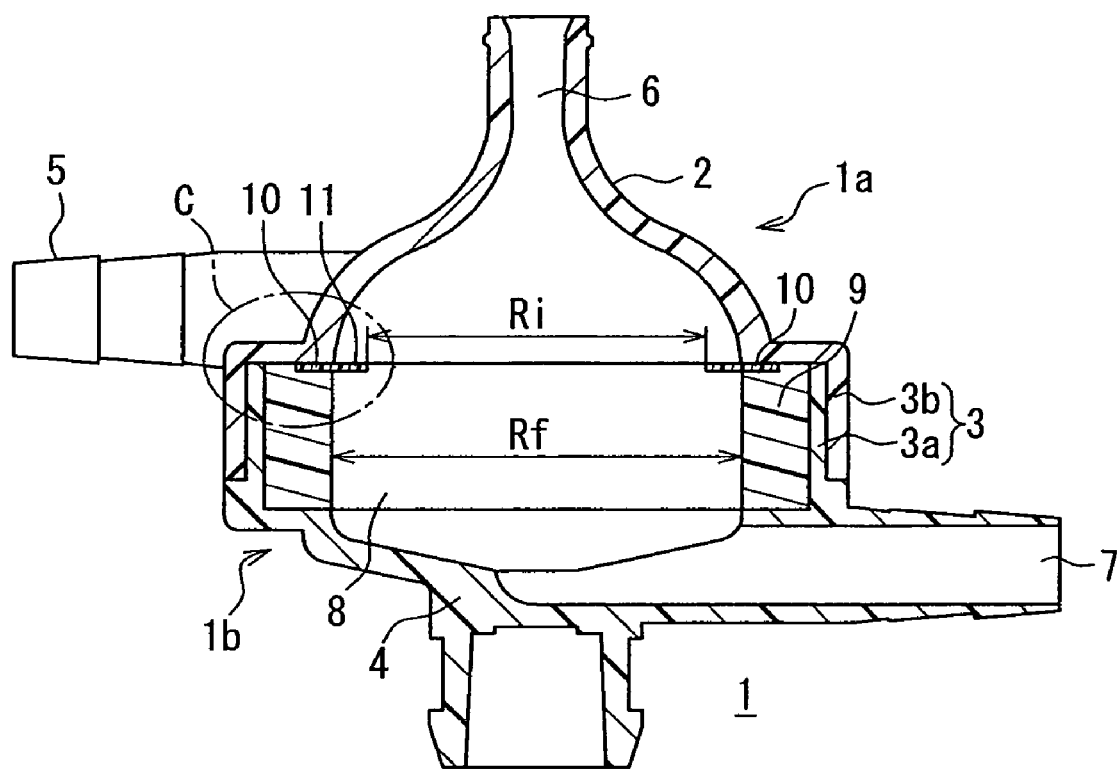
FIG. 8 is a cross-sectional view showing a blood filter device according to Embodiment 2 of the present invention.

The features of the blood filter device in the present embodiment are shown in FIG. 8. The configuration shown in FIG. 8 is substantially the same as what is shown in FIG. 3 except that an annular rib member 10 further is provided. Therefore, the elements common to those as shown in FIG. 3 are applied with the same reference numbers in order to avoid duplicated explanation.

Figure 22:
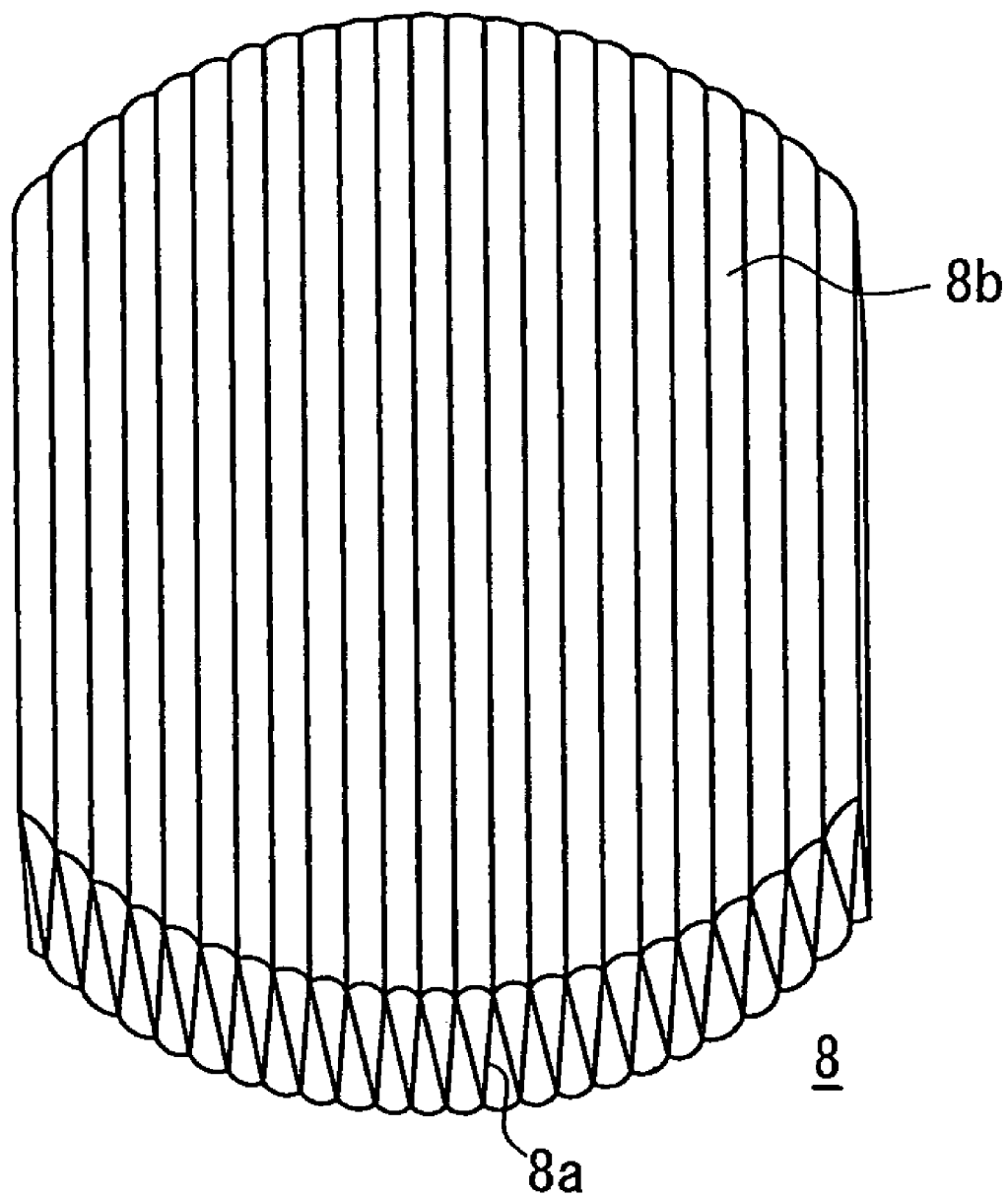
FIG. 22 is a perspective view showing a filter constituting the blood filter device.

The annular rib member 10 shown in FIG. 8 is disposed facing the ridgelines 8b of the pleats of the filter 8 in the outer peripheral region of the filter 8 (see FIG. 22). The inner periphery of the annular rib member 10 extends toward the center of the filter 8 so as to form a regulating plate 11. The regulating plate 11 extends annularly over the outer periphery of the effective region of the filter 8. In FIG. 8, only an annular substrate constituting the annular rib member 10 is shown, but the plurality of ribs (described below) are not shown; The bonding resin is supplied to the region including the outer peripheral part of the filter 8 and the annular rib member 10, and the filter 8 is bonded to the inner peripheral face of the filtration portion 3 with the bonding resin 9.

Figure 9:
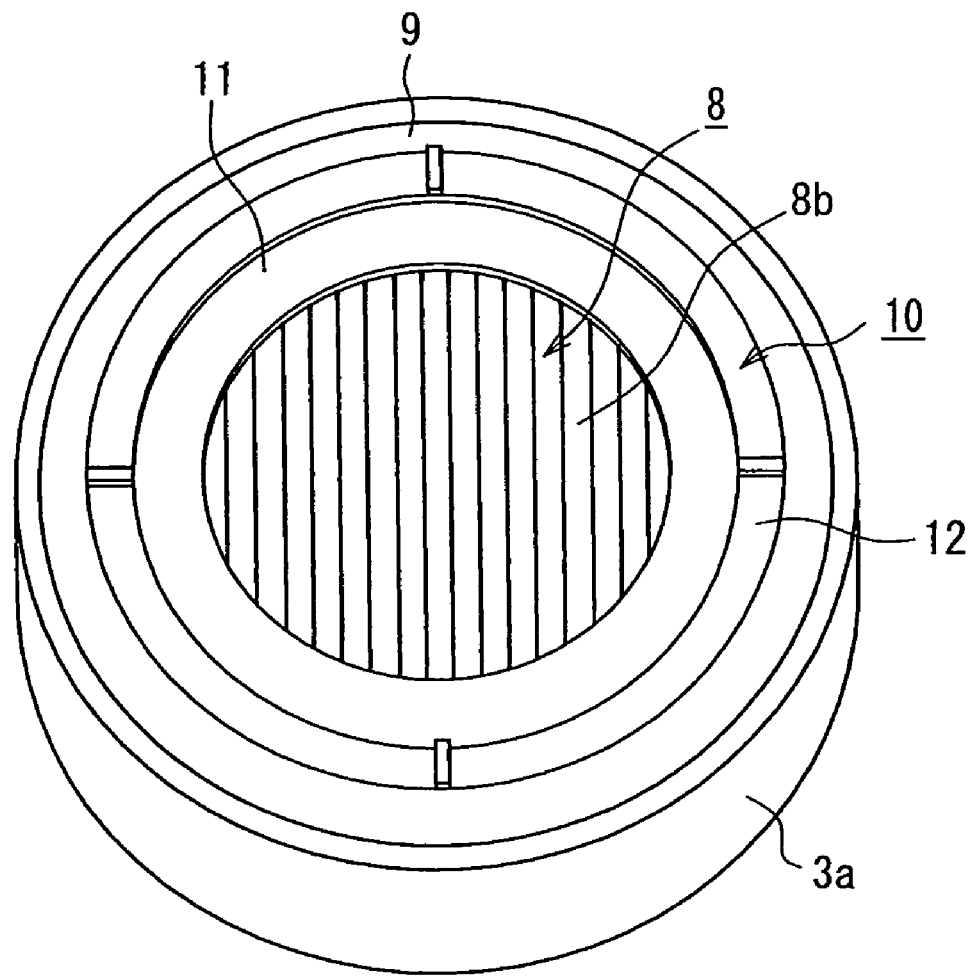
FIG. 9 is a perspective view showing main elements, where a filter is mounted in a housing constituting the blood filter device.

FIG. 9 shows that the annular rib member 10 is mounted in the filter 8, and that the outer periphery of the filter 8 is bonded to the inner peripheral face of the retaining portion inner cylinder 3a with the bonding resin 9. The remaining elements to constitute the lower half 1b together with the retaining portion inner cylinder 3a are not shown in FIG. 9. Numeral 12 denotes the annular substrate constituting the annular rib member 10.

Figure 10:
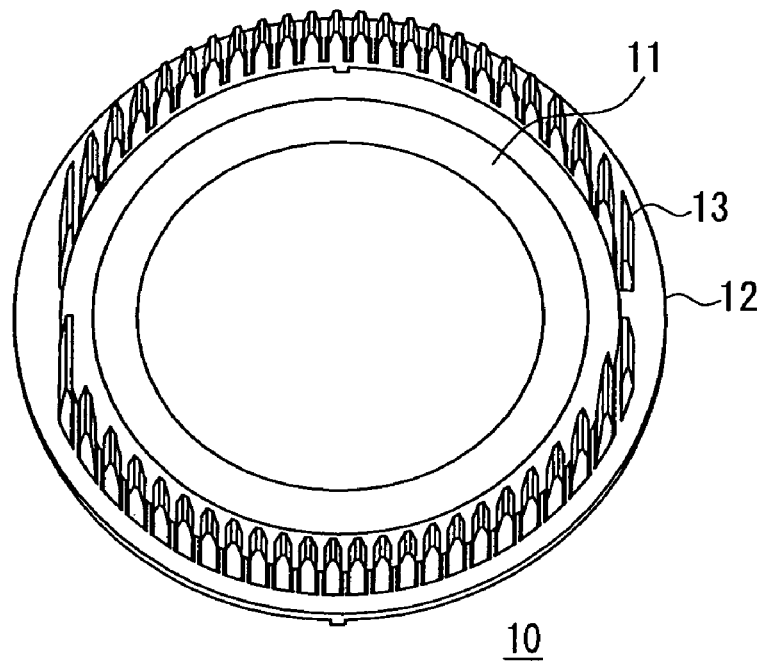
FIG. 10 is a perspective view showing an annular rib member constituting the blood filter device.
Figure 11:
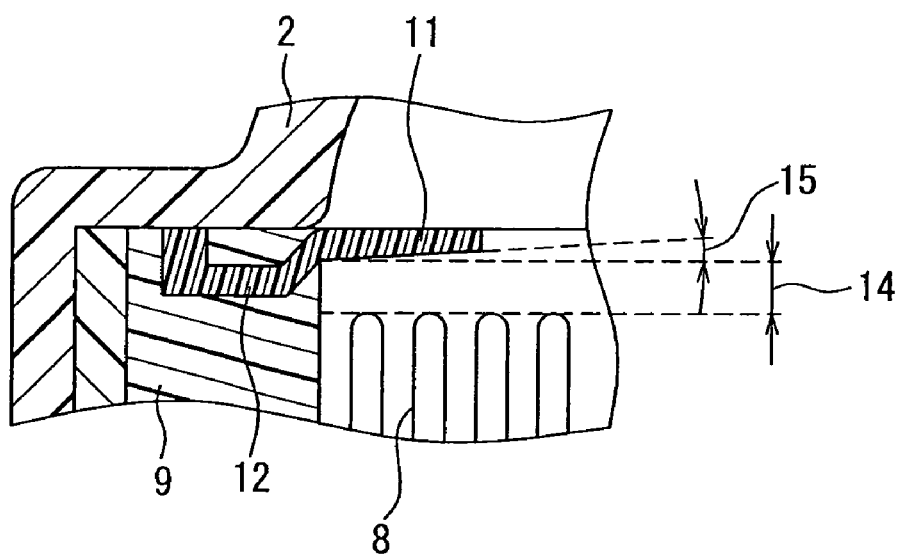
FIG. 11 is a cross-sectional view showing main elements of the annular rib member.

FIG. 10 is a perspective view showing the configuration of the annular rib member 10. The elements are shown in an upside-down state with respect to the state as shown in FIG. 8. The annular rib member 10 is composed of a disc-like annular substrate 12 and a plurality of ribs 13. The plural ribs 13 are aligned on the annular substrate 12 so as to correspond respectively to the gaps between the ridgelines 8b of the pleats in the filter 8. Therefore, the gaps between adjacent ribs 13 correspond to the ridgelines 8b of the respective pleats, and the ridgelines 8b of the pleats are inserted respectively between adjacent ribs 13. As a result of mounting the annular rib member 10, the gaps between the ridgelines 8b of the respective pleats are held by the ribs 13. The regulating plate 11 is formed as a result that the inner periphery of the annular substrate 12 extends toward the center of the filter 8. FIG. 11 shows the cross section of the regulating plate 11.

FIG. 11 is an enlarged view of the region indicated with a circle-C of FIG. 8. For the convenience in reference, the ridgelines of the pleats of the filter 8 are drawn in a state aligned in a perpendicular direction with respect to FIG. 8. The regulating plate 11 is configured so that a clearance 14 is formed between the regulating plate 11 and the ridgelines of the pleats forming the upper face of the filter 8. Further, the lower face of the regulating plate 11 forms a slant 15 with respect to the upper face of the filter 8. The slant 15 is formed in a direction for increasing the clearance 14 toward the center of the filter 8.

Figure 12A:
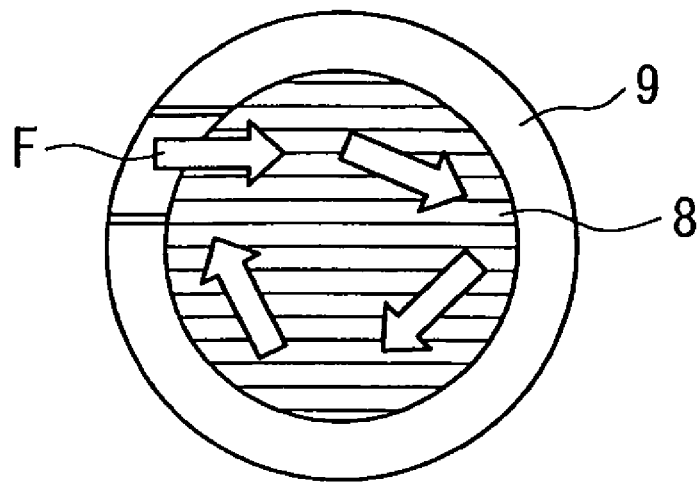
FIG. 12A is a plan view of a filter, for an explanation of a blood flow in the blood filter device.
Figure 12B:
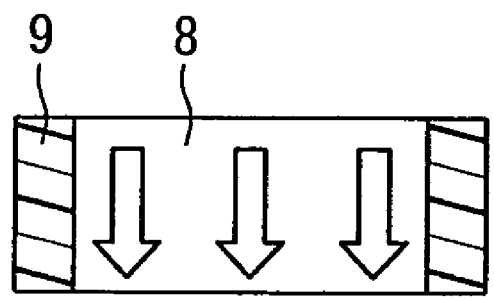
FIG. 12B is a cross-sectional view thereof.

The object for providing the regulating plate 11 in the present embodiment will be described with reference to FIGS. 12A, 12B, and 13A-13C. FIG. 12A is a plan view showing the flow velocity distribution of blood at every part on the filter 8 of the blood filter device, and FIG. 12B is the cross-sectional view. The arrows denote the flow velocities. A wider arrow indicates that the flow velocity is greater in comparison with a narrower arrow. These drawings show a flow velocity distribution in a case where the blood flow in the blood filter device is in an ideal state. Namely, in a plane shown in FIG. 12A, the blood flows in from the blood inlet 5 (see FIG. 8), and then flows annularly along the inner wall into the cavity of the head portion 2, where the flow velocity is uniform in the circumferential direction. As shown in FIG. 12B, even when passing through the cross section of the filter 8, the flow velocity is uniform in the radial direction of the filter 8.

Figure 13A:
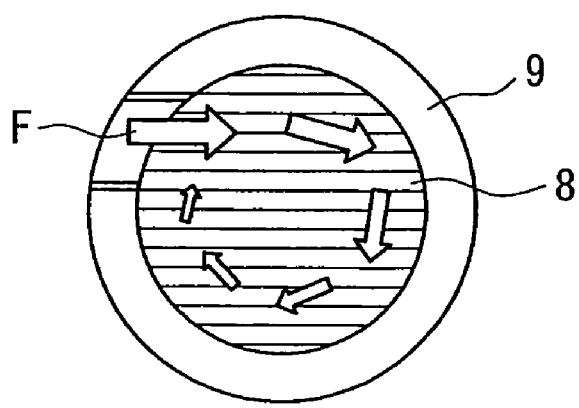
FIG. 13A is a plan view of a filter, for an explanation of a blood flow in a conventional blood filter device.
Figure 13B:
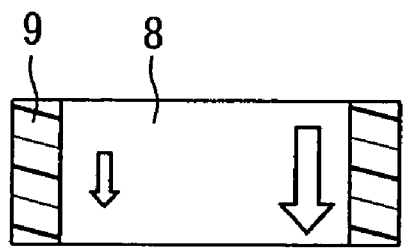
FIG. 13B is a cross-sectional view thereof.

To the contrary, an actual flow velocity falls on a state as shown in FIGS. 13A, 13B. Namely, according to the flow velocity distribution in a plane as shown in FIG. 13A, the blood flowing in from the blood inlet 5 and flowing out immediately from the blood outlet 7 passes through the filter 8 at a high flow velocity. In contrast, the blood that passes through the filter 8 in the midway flowing annularly along the inner wall of the head portion 2 passes through the filter 8 at a low flow velocity. In this manner, as shown in FIG. 13B, a non-uniform current occurs at the time of passing through the cross section of the filter 8.

Figure 13C:
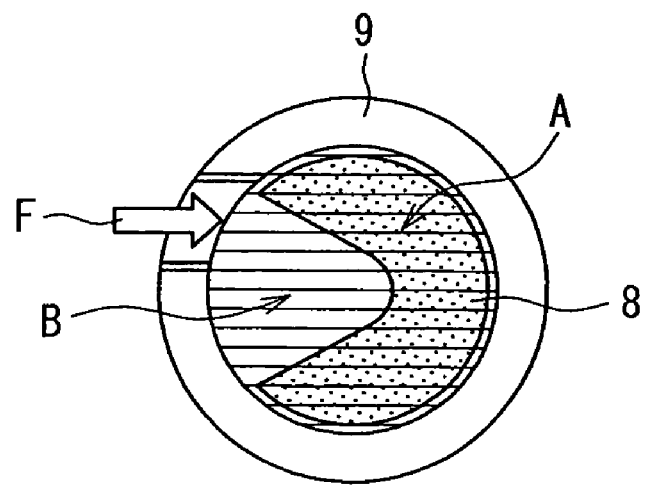
FIG. 13C is a plan view of a filter, for explaining a problem of a blood flow in the conventional blood filter device.

The non-uniform current will cause a problem as shown in FIG. 13C. In FIG. 13C, the region-A indicates coloring of the filter 8, which is caused by hemolysis. In contrast, substantially no coloring is observed in the region-B. This phenomenon seems to depend on the flow velocity of the blood passing through the filter 8. Thus, since the flow velocity of blood is greater at the blood inlet 5 side, the blood is liable to be damaged.

The blood filter device according to the present embodiment can solve the above-noted problem and improve the uniformity in the flow velocity of the blood during the blood passes through the filter. Namely, unlike in the conventional example, the non-uniform current of blood is suppressed by disposing the regulating plate 11, and thus the uniformity in the flow velocity of the blood flow passing through the cross section of the filter 8 will be improved across the filter 8. In other words, the blood flow entering from the blood inlet 5 is hindered by the regulating plate 11 and precluded from immediately flowing out from the blood outlet 7. And the blood flow whose velocity has been lowered by the regulating plate 11 passes through the filter 8 in a state where the channels are dispersed across the filter 8, and flows out from the blood outlet 7. As a result, the flow velocity distribution of the blood passing through the filter 8 approaches the ideal state as shown in FIG. 12B.

For obtaining a sufficient effect in improving the uniformity of the flow, velocity, it is preferable that, when Ri denotes the inner diameter of the annular ring of the regulating plate 11 covering over the outer peripheral part of the filter 8 (see FIG. 8), and Rf denotes the diameter of the effective region of the filter 8 (see FIG. 8), Ri is in a range of $0.7 Rf \leqq Ri \leqq 0.9 Rf$. The effective region of the filter 8 is defined by the inner peripheral face of the supplied bonding resin 10.

The clearance 14 that is formed between the regulating plate 11 and the upper face of the filter 8 and the slant 15 that is provided on the lower face of the regulating plate 11 serve to pass the blood sufficiently through even the outer peripheral part of the filter 8, thereby removing easily the air bubbles in the blood in the clearance region covered with the regulating plate 11.

For allowing the blood flow to pass sufficiently the outer peripheral part of the filter 8, the size of the clearance 14 is in a range of 0.5 mm to 2.0 mm preferably. It is also preferable that the angle of the slant of the lower face of the regulating plate 11 is in a range of 5 degrees to 10 degrees.

In an alternative configuration, the regulating plate 11 can be provided independently of the annular rib member 10.

In the blood filter device of the present embodiment, since the gaps are held between pleats of the filter 8 so as to extend in the ridgeline direction, air bubbles or the like remaining between the pleats are more likely to be removed upward through the gaps. Namely, the air bubbles can be removed easily due to the flow of the blood or the priming liquid entering from the blood inlet 5.

The filter device of the configuration can be produced in the following manner. First, the filter 8 is mounted in the retaining portion inner cylinder 3a of the lower half 1b of the housing. Next, an auxiliary bonding resin is supplied into the space between the outer periphery of the filter 8 and the inner peripheral face of the retaining portion inner cylinder 3a, which then is hardened. Next, the annular rib member 10 is mounted facing the upper face of the filter 8 so that the plurality of ribs 13 are inserted respectively between the ridgelines 8b of the pleats of the filter 8 (see FIG. 22).

(Embodiment 3)

Hereinafter, the method of producing a blood filter device according to Embodiment 3 of the present invention will be described with reference to the attached drawings. The basic configuration of the blood filter device produced by the method according to the present embodiment is substantially the same as what is shown in FIGS. 1-3. Namely, the blood filter device according to the present embodiment has the configuration similar to what is shown in the front view and the plan view of FIGS. 1 and 2. The filter configuration is also similar to what is shown in FIG. 22.

Figure 14:
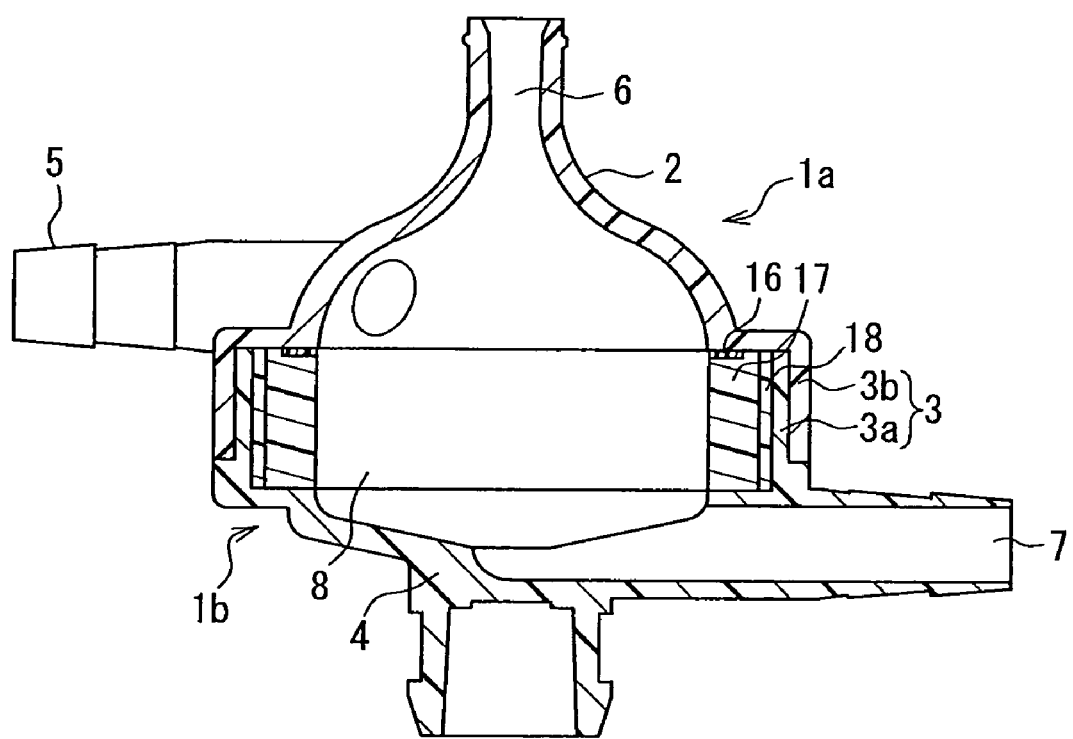
FIG. 14 is a cross-sectional view showing a blood filter device according to Embodiment 3 of the present invention.

FIG. 14 is a cross-sectional view showing a structural example of a blood filter device produced according to the present embodiment. In the configuration shown in FIG. 14, an annular rib member 16 is provided just like in Embodiment 2 of FIG. 8. Though the annular rib member 16 in FIG. 14 is different to some extent from the annular rib member 10 in FIG. 8, a similar configuration can be applied as well in the present embodiment. The basic configuration and effect of the blood filter device in the present embodiment are similar to those of the blood filter device in the previous embodiments, and thus repeated explanation will be avoided.

As shown in FIG. 14, the annular rib member 16 is disposed facing the ridgelines 8b of the plural pleats of the filter 8 in the outer peripheral region of the filter 8. As mentioned below, the annular rib member 16 has a plurality of ribs that are inserted respectively between the ridgelines 8b of the pleats (not shown in FIG. 14). A main bonding resin 17 is supplied to the outer peripheral part of the filter 8 including the annular rib member 16. As mentioned below, the filter 8 is bonded temporarily to the cavity of the filtration portion 3 with an auxiliary bonding resin 18, and further bonded to the inner peripheral face of the filtration portion 3 with the main bonding resin 17.

Figure 15:
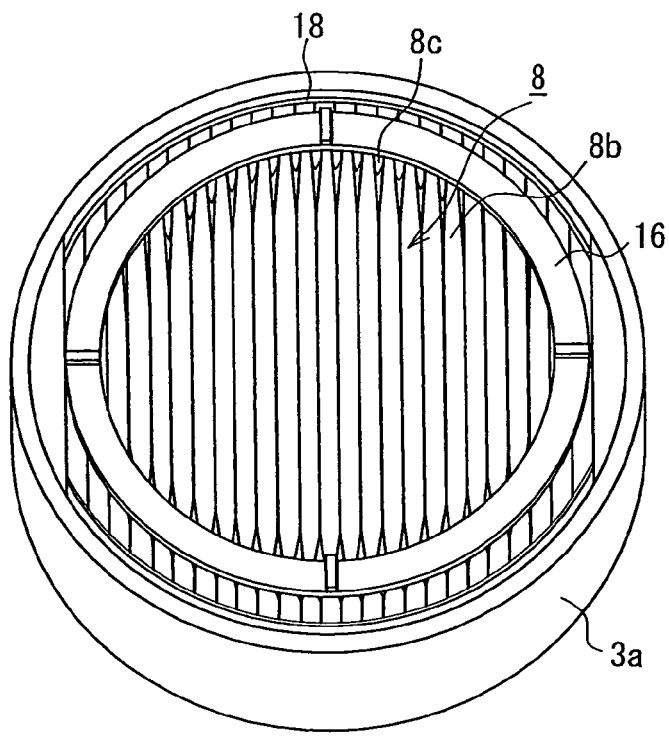
FIG. 15 is a perspective view showing main elements, where a filter is mounted in a housing constituting the blood filter device.

FIG. 15 shows a state where the annular rib member 16 is mounted in the filter 8, and the outer periphery of the filter 8 is temporarily bonded to the inner peripheral face of the retaining portion inner cylinder 3a with the auxiliary bonding resin 18. In this drawing, the remaining elements constituting the lower half 1b together with the retaining portion inner cylinder 3a are not shown.

Figure 16:
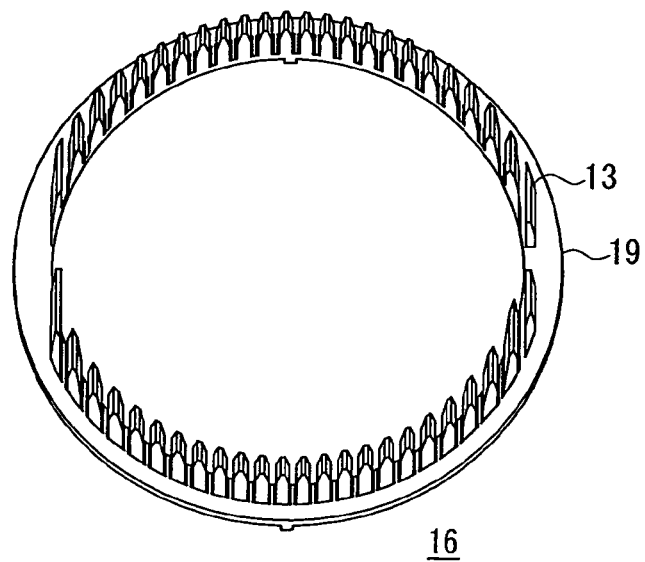
FIG. 16 is a perspective view showing an annular rib member constituting the blood filter device.

FIG. 16 is a perspective view showing the configuration of the annular rib member 16. The annular rib member 16 consists of a disc-like annular substrate 19 and a plurality of ribs 13. The ribs 13 are aligned on the annular substrate 19 and correspond respectively to the gaps between the ridgelines 8b of the filter 8. As a result, the gaps between adjacent ribs 13 correspond to ridgelines 8b of the respective pleats, and thus the ridgelines 8b of the pleats are inserted respectively between adjacent ribs 13 as shown in FIG. 15.

As shown in FIG. 15, due to the mounted annular rib member 16, the gaps between the ridgelines 8b of the respective pleats are widened by the ribs 13 in the peripheral region of the filter 8 so as to form pleat-gaps 8c. Further, as a result of supplying and hardening the main bonding resin 17 by the producing method of the present embodiment as described below, an outward tensile force is applied to the both ends of each pleat, thereby the pleat-gaps 8c formed by the ribs 13 are widened from the peripheral region of the filter 8 to the central region so as to increase the gap volume between the pleats.

In the thus configured blood filter device, since gaps extending in the ridgeline direction are held between the pleats of the filter 8, the air bubbles remaining between the pleats can be removed easily upward through the gaps. Namely, the air bubbles can be removed easily due to the flow of the blood or the priming liquid flowing from the blood inlet 5. All of the gaps between the pleats of the filter 8 are not necessarily formed in the ridgeline direction, but corresponding effects can be obtained if the gaps are widened over the initial peripheral region of the filter 8. Needless to note, it is the most effective if all of the gaps are directed in the ridgeline direction of the pleats.

It is desirable that the filter 8 shaped like a disc by arranging a plurality of pleats in parallel as described above is retained in the filtration portion 3 in the state where there are certain gaps between adjacent pleats. When the pleats 8 are in contact with each other and there is no gap therebetween, a closed space is formed at the bottom of a valley between the pleats. Therefore, if air bubbles remaining in or air bubbles formed at other places get trapped in the closed space, it is difficult to remove the air bubbles even by applying a physical impact to the housing. The difficulty in removal of air bubbles will result in deterioration in the priming efficiency.

However, it is difficult to fix the filter 8 in the cavity of the filtration portion 3 in a state of holding gaps between adjacent pleats. That is, when the filter 8 folded to have pleats is mounted in the filtration portion 3, the pleats bulge because the filter sheet forming the filter 8 is in a free state. Thus, adjacent pleats are liable to be in contact with each other. This can be a problem especially when the efficiency of filtering is to be increased without increasing the size of the housing of the filter. That is, if the pleat height is increased and the pitches are made fine to increase the area of a filter film, the pleats are liable to contact with each other at their natural bulges.

Figure 17:
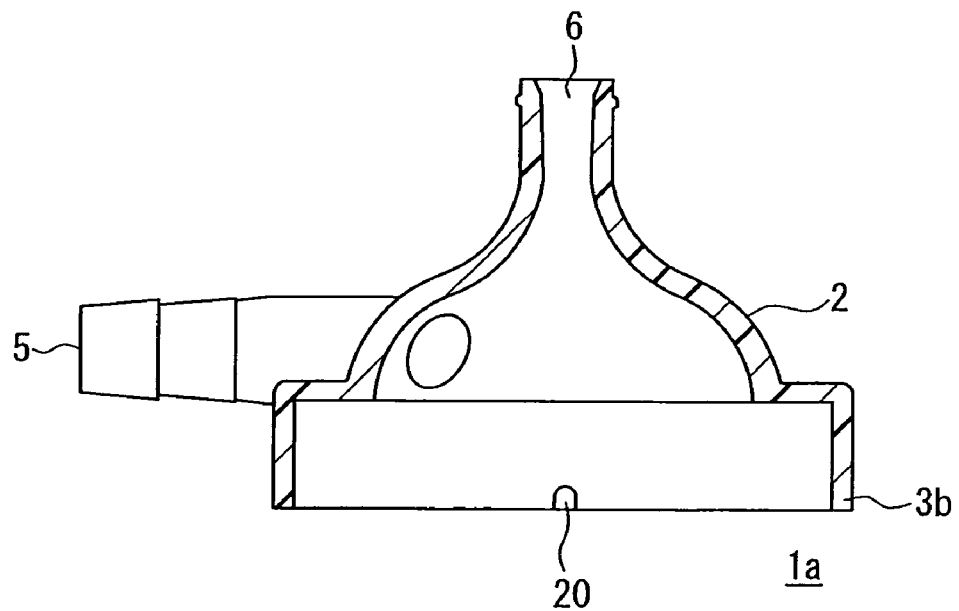
FIG. 17 is a cross-sectional view showing an upper half of the housing constituting the blood filter device.
Figure 18:
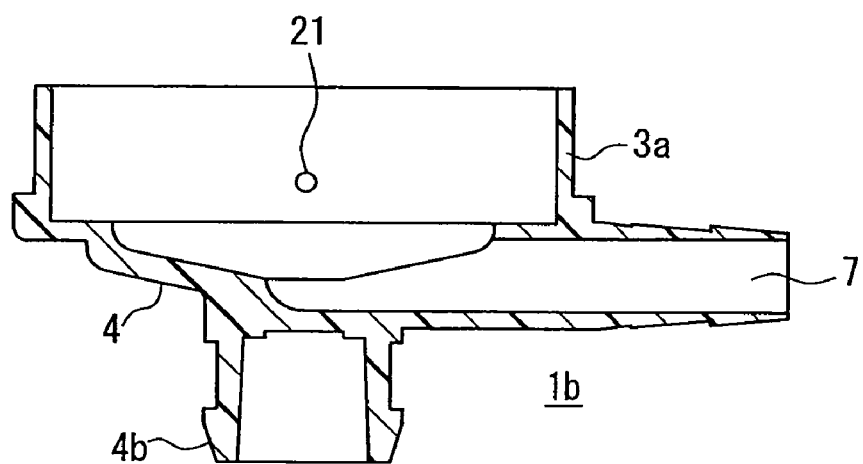
FIG. 18 is a cross-sectional view showing a lower half of the housing constituting the blood filter device.

The method of producing a blood filter device in the present embodiment serves to maintain easily the state where gaps are held between pleats of the filter. Hereinafter, the method of producing a filter device of the present embodiment will be described. FIG. 17 is a cross-sectional view showing the upper half 1a of housing constituting the blood filter device, and FIG. 18 is a cross-sectional view showing the lower half 1b of housing.

The basic configuration is as described with reference to FIGS. 1-3. A pair of notches 20 are formed on the retaining portion outer cylinder 3b of the upper half 1a of the housing. Through holes 21 are formed on the retaining portion inner cylinder 3a of the lower half 1b of the housing, at the positions corresponding to the pair of notches 20 on the retaining portion outer cylinder 3b. When the upper half 1a of the housing is fit into the lower half 1b of the housing, the notches 20 communicate with the through holes 21, thereby forming holes that penetrate peripheral walls of the retaining portion inner and outer cylinders 3a and 3b. These holes are used as resin channels for supplying a resin during potting, which will be described below.

First, the filter 8 is mounted in the retaining portion inner cylinder 3a of the lower half 1b of the housing as shown in FIG. 15. Then, the auxiliary bonding resin 18 is supplied into the space between the outer periphery of the filter 8 and the inner peripheral face of the retaining portion inner cylinder 3a and is hardened. Subsequently, an annular rib member 16 is disposed facing the upper face of the filter 8 so that the plurality of ribs 13 are inserted respectively between the ridgelines of the plurality of pleats of the filter 8. Thereby, as shown in FIG. 15, pleat-gaps 8c are formed at least on the outer peripheral part of the filter 8.

Next, the retaining portion inner cylinder 3a of the lower half 1b of the housing to which the filter 8 is temporarily bonded in, the above manner is fit into the retaining portion outer cylinder 3b of the lower half 1a of the housing shown in FIG. 17, thereby integrating the housing 1. Subsequently, the housing 1 in which the filter 8 is mounted is placed in a device provided with a potting jig as shown in FIG. 19 so as to carry out potting with a sealing resin.

Figure 19:
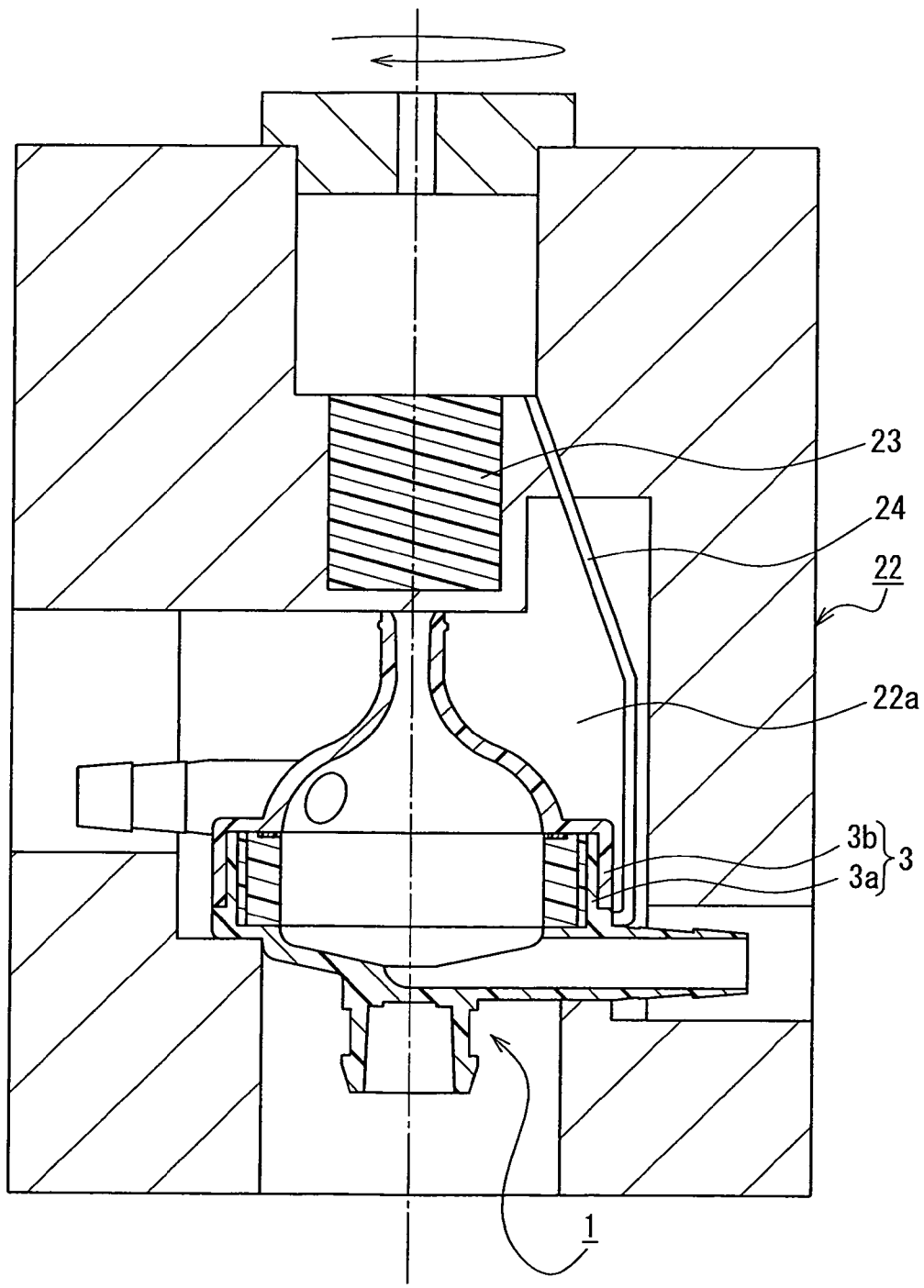
FIG. 19 is a cross-sectional view showing a potting device used in the method of producing the blood filter device in an embodiment of the present invention.

The device shown in FIG. 19 is composed of a rotating jig 22, a resin reservoir 23, and a resin supply channel 24. The rotating jig 22 has a cavity 22a having a prescribed shape for supporting the housing 1. The resin reservoir 23 storing a sealing resin such as a urethane resin is provided at the top of the rotating jig 22, and the resin supply channel 24 is formed from the resin reservoir 23 to the lateral face of the filtration portion 3. By placing the housing 1 in the rotating jig 22 and rotating the rotating jig 22, the housing 1 rotates together. A sealing resin supplied to the lateral face of the filtration portion 3 enters into the cavity of the retaining portion inner cylinder 3a through the notches 20 and the through holes 21 (see FIGS. 17 and 18).

When the rotating jig 22 is rotated, a horizontal centrifugal force around the central axis of the filtration portion 3 acts. As a result, the sealing resin spills out of the resin reservoir 23 so as to be supplied to the retaining portion outer cylinder 3b through the resin supply channel 24, so that the resin is supplied into the space between the inner peripheral face of the retaining portion inner cylinder 3a and an outer peripheral part of the filter 8. By hardening the supplied resin, the filter 8 can be retained on the inner peripheral face of the retaining portion inner cylinder 3a with the main bonding resin 17 as shown in FIG. 14.

Figure 20:
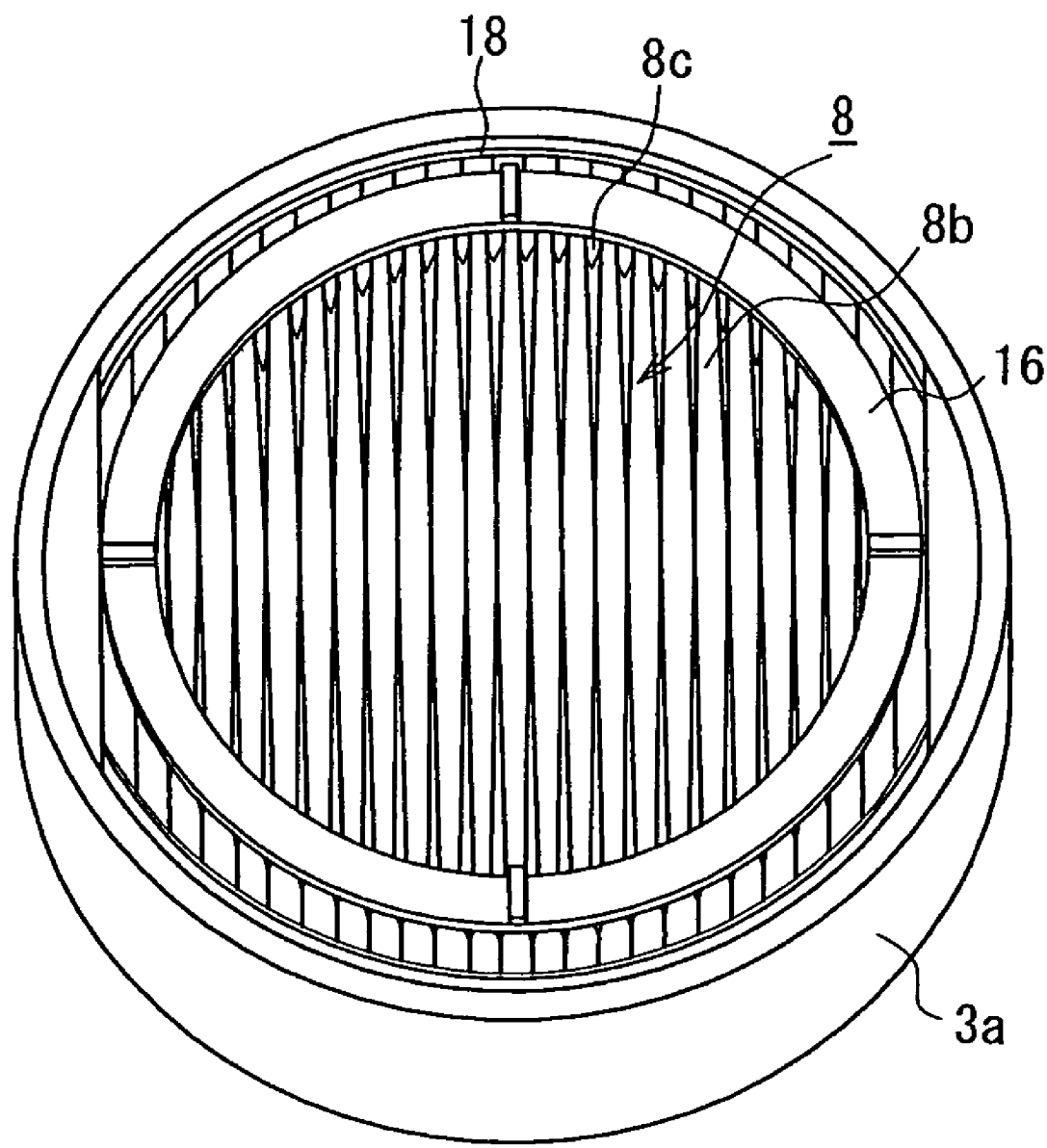
FIG. 20 is a perspective view showing main elements of the filter, for showing the effect provided by the producing method.
Figure 21:
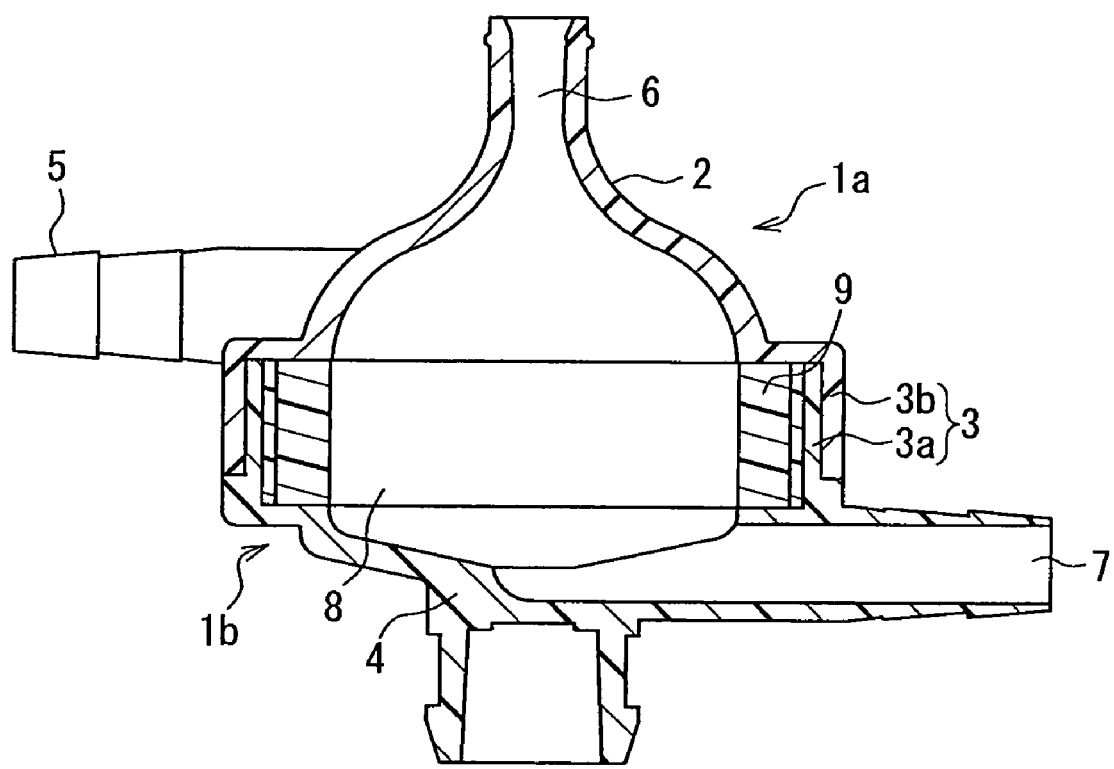
FIG. 21 is a cross-sectional view showing a conventional blood filter device.

The step of supplying and hardening the main bonding resin 17 is carried out at a temperature in a predetermined range higher than room temperature. Therefore, when the main bonding resin 17 is allowed to cool to room temperature, shrinkage of the resin generates an outward tensile force applied to the both ends of each of the pleats of the filter 8. As a result, the pleat-gaps 8c formed by the ribs 13 of the annular rib member 16 shown in FIG. 15 will be widened from the peripheral region of the filter 8 to the central region so as to increase the gap volume between the pleats as shown in FIG. 20.

For obtaining such effects without fail, it is important to set relationships in the coefficients of thermal expansions of the filter, the potting resin and the housing. For instance, it is required to set appropriately the relationships in the coefficients of thermal expansions of the housing 1, the filter 8 and the main bonding resin 17. Namely, materials are selected to make the coefficients of thermal expansion of the main bonding resin 17 be greater than that of the housing material. In the combination of the materials for the housing and the main bonding resin, for example, polycarbonate can be used for the housing 1 and urethane resin can be used for the main bonding resin 17. In such a case, the main bonding resin 17 is supplied to have a thickness in a range of 5 to 10 mm in the radial direction of the filtration portion 3 so as to obtain a thermal shrinkage force suitable for increasing the gap volume between the pleats.

It is also preferable that the step of supplying and hardening the main bonding resin 17 is carried out at a temperature in a range of 35 to 55° C. When the temperature is too low, sufficient thermal shrinkage cannot be obtained. When the temperature is too high, the thermal shrinkage force may be too strong, and the inner face of the housing 1 and the main bonding resin 17 may be peeled off.

It is recommended that the range for supplying with the main bonding resin 17 be adjusted on the basis of the inner periphery of the annular rib member 16. The inner periphery of the annular rib member 16 is set to coincide with the diameter of the lower end of the inner peripheral face of the head portion 2 and also with the diameter of the upper end of the inner peripheral face of the bottom portion 4. Accordingly, a channel in the filter 8 defined by the main bonding resin 17 continues smoothly from the lower edge of the inner peripheral face of the head portion 2 to the upper end of the inner peripheral face of the bottom portion 4, and thus an excellent channel condition is obtained.

Industrial Applicability

Since the blood filter device of the present invention is small, and it maintains sufficient filtration performance and suppresses sufficiently the pressure loss, and thus it is useful as a component of an artificial heart-lung circuit.

The invention claimed is:

1. A blood filter device comprising:
a housing that includes a head portion provided with a blood inlet and forming an upper structure of the housing, a filtration portion positioned below the head portion and forming a middle structure of the housing, and a bottom portion disposed below the filtration portion and provided with a blood outlet; and
a filter mounted in a cavity of the filtration portion and partitioning a cavity of the housing into a head portion side and a bottom portion side,
the filter being formed of a filter sheet folded to have a plurality of pleats, and disposed so that ridgelines of the plurality of pleats traverse respectively the cavity of the filtration portion in parallel,
wherein the bottom portion has a conical portion on the inner bottom face protruding downward to form a conical face, and
an annular regulating plate is provided above an outer peripheral part of an effective region of the filter, so as to cover over the outer peripheral part of the effective region, with a clearance being provided between an upper face of the filter and a lower face of the regulating plate.

2. The blood filter device according to claim 1, wherein the conical face has a base angle $\theta$ being set in a range of $6° \leq \theta \leq 12°$.

3. The blood filter device according to claim 1, wherein the bottom portion has a cylindrical portion connected to the filtration portion, and the conical portion is formed at the lower part of the cylindrical portion.

4. The blood filter device according to claim 3, wherein the height of the cylindrical portion is at least 0.5 mm.

5. The blood filter device according to claim 1, wherein the diameter $\phi$ of the cavity of the filtration portion is set in a range of 35 mm $\leq \phi \leq$ 65 mm.

6. The blood filter device according to claim 1, comprising an annular rib member formed by providing a plurality of ribs on an annular substrate disposed facing the ridgelines of the pleats in the outer peripheral region of the filter,
the plural ribs are inserted respectively between adjacent pleats of the filter sheet so as to hold gaps on the filter sheets, and
the inner periphery of the annular substrate extends toward the center of the filter so as to form the regulating plate.

7. The blood filter device according to claim 1, wherein when Ri denotes an inner diameter of an annular ring of the regulating plate covering over the outer peripheral part of the filter and Rf denotes the diameter of the effective region of the filter, Ri is in a range of 0.7 Rf $\leq$ Ri $\leq$ 0.9 Rf.

8. The blood filter device according to claim 1, wherein the clearance is in a range of 0.5 mm to 2.0 mm.

9. The blood filter device according to claim 1, wherein the lower face of the regulating plate is slanted with respect to the upper face of the filter, and the slant is formed so that the clearance is increased toward the center of the filter.

10. The blood filter device according to claim 9, wherein the slant angle of the lower face of the regulating plate is in a range of 5 degrees to 10 degrees.

11. A method of producing a blood filter device, the blood filter device comprising:
a housing that includes a head portion provided with a blood inlet and forming an upper structure of the housing, a filtration portion positioned below the head portion and forming a middle structure of the housing, and a bottom portion disposed below the filtration portion and provided with a blood outlet; and
a filter mounted in a cavity of the filtration portion and partitioning a cavity of the housing into a head portion side and a bottom portion side,
the filter being formed of a filter sheet folded to have a plurality of pleats, and disposed so that ridgelines of the plurality of pleats traverse respectively the cavity of the filtration portion in parallel, the method comprising:

mounting the filter in the filtration portion of the housing where the bottom portion has a conical portion on the inner bottom face protruding downward to form a conical face, and bonding the outer peripheral part of the filter to the filtration portion with an auxiliary bonding resin, mounting an annular rib member in a vicinity of the filter, the annular rib member including an annular substrate and a plurality of ribs aligned in a circumferential direction thereon, so that the ribs are inserted respectively between the ridgelines of the pleats in an outer peripheral region of the filter, thereby forming gaps between adjacent pleats of the filter sheet in the outer peripheral region of the filter, supplying a main bonding resin into a space between the outer peripheral part of the filter and the inner peripheral face of the filtration portion and hardening at a temperature higher than room temperature so as to bond the filter to the filtration portion with the main bonding resin, and applying an outward tensile force to the both ends of each of the pleats due to shrinkage of the main bonding resin allowed to cool to room temperature, wherein an inner periphery of the annular substrate is extended toward a center of the filter, thereby forming an annular regulating plate, and when the annular rib member is mounted on the filter, the annular regulating plate is arranged above an outer peripheral part of an effective region of the filter, so as to cover over the outer peripheral part of the effective region of the filter, with a clearance being provided between an upper face of the filter and a lower face of the regulating plate.

12. The method of producing a blood filter device according to claim 11, wherein the housing is formed of polycarbonate resin, and urethane resin is used for the main bonding resin that is supplied to have a thickness in a range of 5 to 10 mm in the radial direction of the filtration portion.

13. The method of producing a blood filter device according to claim 12, wherein the main bonding resin is hardened at a temperature in a range of 35 to 55° C.

14. The method of producing a blood filter device according to claim 11, wherein the main bonding resin is supplied up to a region including the annular rib member.

15. The method of producing a blood filter device according to claim 11, wherein the main bonding resin is supplied into the space between the outer peripheral part of the filter and the inner peripheral face of the filtration portion while applying a centrifugal force about the center of the cavity of the filtration portion.

* * * * *